(12) United States Patent
Karlsson et al.

(10) Patent No.: US 9,827,380 B2
(45) Date of Patent: Nov. 28, 2017

(54) CAP ASSEMBLY

(71) Applicant: SHL Group AB, Nacka Strand (SE)

(72) Inventors: Sebastian Karlsson, Sundbyberg (SE); Mattias Daniel, Stockholm (SE)

(73) Assignee: SHL Group AB, Nacka Strand (SE)

( * ) Notice: Subject to any disclaimer, the term of this patent is extended or adjusted under 35 U.S.C. 154(b) by 522 days.

(21) Appl. No.: 14/365,636

(22) PCT Filed: Dec. 7, 2012

(86) PCT No.: PCT/SE2012/051358
§ 371 (c)(1),
(2) Date: Jun. 15, 2014

(87) PCT Pub. No.: WO2013/089616
PCT Pub. Date: Jun. 20, 2013

(65) Prior Publication Data
US 2014/0343507 A1   Nov. 20, 2014

Related U.S. Application Data

(60) Provisional application No. 61/570,930, filed on Dec. 15, 2011.

(30) Foreign Application Priority Data

Dec. 15, 2011   (SE) ..................................... 1151198

(51) Int. Cl.
*A61M 5/32* (2006.01)
*A61M 5/24* (2006.01)
*A61M 5/34* (2006.01)

(52) U.S. Cl.
CPC ........ *A61M 5/3202* (2013.01); *A61M 5/2466* (2013.01); *A61M 5/3204* (2013.01); *A61M 5/347* (2013.01)

(58) Field of Classification Search
CPC .............. A61M 5/3202; A61M 5/3204; A61M 5/3213; A61M 39/20; A61M 2005/312; A61M 5/347
(Continued)

(56) References Cited

U.S. PATENT DOCUMENTS 3,835,862 A * 9/1974 Villari .................... A61M 39/20
138/89
6,517,517 B1 * 2/2003 Farrugia .............. A61M 5/2033
604/131
(Continued)

FOREIGN PATENT DOCUMENTS

EP   1483004 B1   12/2004
EP   2021057 B1   2/2009

OTHER PUBLICATIONS

Sweden Patent Office, Int'l Search Report in PCT/SE2012/051358, Mar. 13, 2013.
(Continued)

*Primary Examiner* — Gerald Landry, II
(74) *Attorney, Agent, or Firm* — Piedmont Intellectual Property

(57) ABSTRACT

A cap assembly for a medicament delivery device having a housing and a medicament container holder. The cap assembly includes a retainer member connectable to the container holder; a hub having a needle and coaxially movable within the retainer member; an inner cap connected to the hub and the retainer member; an outer cap coaxially arranged to the inner cap; and a cap clutch mechanism having a locking member that is axially movable in relation to the inner and outer caps between a disengaged position, in which the outer cap is rotatable relative to the inner cap, and an engaged position, in which the outer cap is rotationally locked to the inner cap. The cap clutch mechanism also has a clutch
(Continued)

biasing device arranged between the outer cap and the locking member for biasing the locking member for keeping it in the disengaged position.

19 Claims, 9 Drawing Sheets

(58) Field of Classification Search
USPC .................. 604/192, 198, 232, 256, 263
See application file for complete search history.

(56) References Cited

U.S. PATENT DOCUMENTS

| 7,771,397 B1* | 8/2010 | Olson | A61M 5/3202 |
| | | | 604/192 |
| 8,708,968 B2* | 4/2014 | Julian | A61M 5/20 |
| | | | 604/192 |
| 2003/0014018 A1* | 1/2003 | Giambattista | A61M 5/002 |
| | | | 604/198 |
| 2005/0049561 A1* | 3/2005 | Hommann | A61M 5/3202 |
| | | | 604/263 |
| 2005/0101912 A1* | 5/2005 | Faust | A61M 5/158 |
| | | | 604/117 |
| 2005/0203466 A1* | 9/2005 | Hommann | A61M 5/2033 |
| | | | 604/240 |
| 2005/0283114 A1* | 12/2005 | Bresina | A61M 5/158 |
| | | | 604/93.01 |
| 2007/0129674 A1* | 6/2007 | Liversidge | A61M 5/326 |
| | | | 604/110 |
| 2008/0154192 A1* | 6/2008 | Schraga | A61M 5/50 |
| | | | 604/110 |
| 2009/0030376 A1* | 1/2009 | Teufelberger | A61M 5/2466 |
| | | | 604/188 |
| 2011/0118667 A1* | 5/2011 | Zaiken | A61M 5/3202 |
| | | | 604/138 |
| 2012/0265136 A1* | 10/2012 | Lawlis | A61K 38/24 |
| | | | 604/110 |

OTHER PUBLICATIONS

Sweden Patent Office, Written Opinion in PCT/SE2012/051358, Mar. 13, 2013.

* cited by examiner

CAP ASSEMBLY

TECHNICAL AREA

The present invention relates to a cap assembly for a medicament delivery device and in particular a cap assembly for injection needle protection comprising an outer and an inner cap, having an enhanced safety aspect when exposed to external forces.

BACKGROUND OF INVENTION

For many injection devices intended for self-administration of medicament, it is often desirable that the device is as complete as possible, i.e. that the number of operations or assembly steps needed in order to make the device ready to deliver a dose of medicament is minimized.

One solution for keeping a medicament delivery device as pre-assembled as possible is to deliver the medicament delivery device with a delivery member, such as a needle, pre-attached. This solution often causes the rear end of the needle to protrude into the interior of the container, which could be a drawback if the medicament reacts with the material of the delivery member when exposed for a period of time. In that respect it would be desirable to have the rear part of the delivery member outside the container until the delivery is to be performed.

On the other hand, the front part of the delivery member has to be protected before use in order to prevent unintentional needle sticks and in order to keep the needle clean. The front end of the delivery member is therefore often arranged with a sheath and/or a cap that has to be removed beforehand.

In order to accomplish the above in a simple and effective way, the applicant has developed a cap assembly that comprises a retainer member connectable to a medicament container holder of a medicament delivery device. The cap assembly further comprises a hub coaxially movable within the retainer member where the hub comprises a needle having a proximal end and a distal end. An inner cap is interactively connected to the hub and the retainer member. The engagement between the outer cap and the inner cap and between the inner cap and the retainer member is configured such that removal of the outer cap causes the hub to move distally such that the distal end of the needle penetrates the proximal end of the medicament container.

The cap assembly also comprises a safety feature comprising an outer cap clutch provided between the outer cap and the housing of the medicament delivery device where the clutch is set in engagement when the outer cap is actively moved towards the housing. The outer cap clutch is further arranged to prevent the user from applying an excessive force in the wrong direction when removing the outer cap from the cap assembly. Thus, the cap clutch ensures that the outer cap is not accidentally removed without the active safety operation, and that it is correctly removed in the right rotational direction.

The above design has proven to work well in most cases. However, it has been noticed that if the device is subjected to sudden external forces, such as a drop of the device onto a surface or vibrations during transport, to mention a few, then the cap clutch may be moved such that it becomes engaged even without the active movement of the outer cap in relation to the housing. This may in turn enable removal of the outer cap without the safety operation of moving the outer cap towards the housing.

BRIEF DESCRIPTION OF INVENTION

In order to overcome one or several of the above-mentioned problems, a cap assembly for a medicament delivery device according to independent claim 1 is provided.

Further aspects, improvements and variations are disclosed in the dependent claims, the figures and the description.

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

According to a main aspect of the invention, it comprises a cap assembly for a medicament delivery device where the medicament delivery device may comprise a housing and a medicament container holder.

The cap assembly according to the present invention may comprise a retainer member connectable to the medicament container holder. It is of course feasible that the retainer member is connected to some other fixed structure of the medicament delivery device adjacent the medicament container.

The cap assembly according to the present invention may further comprise a hub, which may be coaxially movable within the retainer member. The hub may preferably comprise a needle having a proximal end and a distal end. Further a removable inner cap may be interactively connected to the hub and to the retainer member. Also a removable outer cap is coaxially arranged to the inner cap. This design enables activation and connection of the injection needle with the medicament container when the outer cap is operated because also the inner cap is operated and thereby the hub.

The cap assembly may further preferably comprise a cap clutch mechanism comprising a locking member which is axially movable in relation to said inner and outer caps between a disengaged position in which said locking member is disconnected from the outer and the inner cap such that the outer cap is rotatable in relation to said inner cap and an engaged position in which said locking member is connected to the outer and to the inner cap such that the outer cap is rotationally locked to the inner cap. The cap clutch mechanism further comprises clutch biasing means arranged between the outer cap and the locking member, said clutch biasing means being capable of biasing the locking member for keeping it in the disengaged position.

With the cap clutch mechanism having clutch biasing means it is ensured that there is a safety feature for enabling removal of the caps and thereby exposure of the injection needle by an active operation by a user, and on the other hand an assertion that the safety feature will not be set aside or rendered non-functional by external forces such as sudden impacts, vibrations or the like.

The locking member comprises first engagement members operationally intended to interact with corresponding second engagement members on said outer cap, when the locking member is in the engaged position. Said first and said second engagement members are designed to allow engagement between the outer cap and the inner cap in one rotational direction only. Said first engagement member comprises wedge-shaped protrusions on said locking member and said second engagement member comprises a ratchet on said outer cap. The ratchet is positioned on the inner surface of the outer cap, preferably near the distal end. The locking member is ring-shaped and the wedge-shaped protrusions are positioned on the outer surface of the locking member. This function ensures that a user cannot cause damage to the device even if handled wrongly because the outer cap can only function as to be removed by rotation in one direction only. If turned in the other direction, nothing will happen apart from that the outer cap will rotate wherein the wedge-shaped protrusions will merely slide over the ratchet.

The locking member further comprises a passage provided with a number of first planar surfaces, and the inner cap is arranged with a number of second planar surfaces on its outer surface, where said first and said second planar surfaces form a rotational lock when the locking member is in the engaged position. The first planar surfaces are positioned on the inner surface of the locking member. This feature provides an active safety feature in that the user has to bring the engagement members into contact with each other in order to be able to remove the caps.

On the other hand said clutch biasing means is a resilient member comprising a distal end connectable to the locking member and a proximal end connectable to the outer cap. The distal end of the resilient member is preferably fixedly connected to the locking member and the proximal end of the resilient member is preferably configured to abut against an abutting surface on the inner surface of the outer cap. Further, the resilient member has preferably a spiral shape and is preferably integral with the locking member. The resilient member keeps said locking member in the disengaged position, i.e. the resilient member urges the locking member out of engagement with said outer cap, whereby it is ascertained that any external force acting on and displacing said locking member into engagement with said outer cap, will return the locking member to the disengaged position after the external force has been removed or ended, e.g. when by accident the device is dropped.

It is of course to be understood that other components and members may be utilized that are capable of performing the desired function.

The cap assembly further comprises a shield front connectable to a proximal end of an axially movable shield sleeve of the medicament delivery device.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
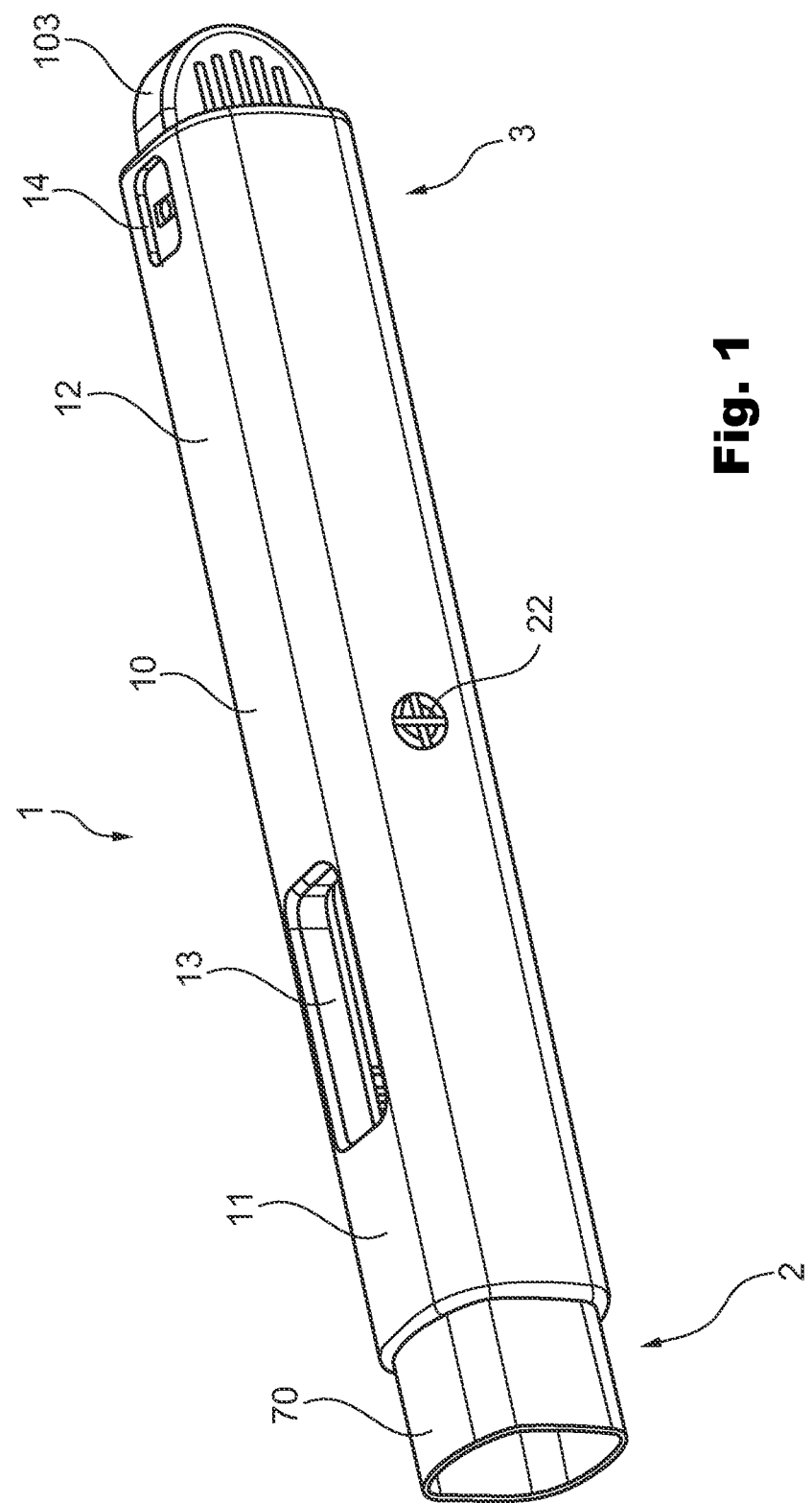
FIG. 1 shows a perspective view of a non-limiting example of a medicament delivery device with which the present invention may be used.

FIG. 1 shows a perspective view of a non-limiting example of a medicament delivery device 1 to which a cap assembly according to the present invention may be attached and used. The non-limiting medicament delivery device 1 has a proximal end 2 and a distal end 3 and comprises a housing 10 having a proximal part or end 11 and a distal part or end 12. The housing extends along a longitudinal axis. In the assembled state of the medicament delivery device 1, the housing 10 forms the outer surface or appearance of the medicament delivery device 1. In the perspective view of FIG. 1, the medicament delivery device 1 is not yet fully assembled, and an axially movable shield sleeve 70 projects from the proximal end of the housing 10. The shield 70 being longitudinally and resiliently movable within the housing. Full assembly of the medicament delivery device 1 is described in more detail below, for example with reference to FIG. 3.

The housing 10 of the medicament delivery device 1 comprises a window 13 that allows the user to view the progress of medicament delivery, i.e. whether the medicament delivery device 1 is still in its initial stage with the medicament not yet being injected, or whether the medicament container is already emptied. Through window 13, the user can see the medicament container accommodated at least in the proximal part of the housing 10. In a preferred embodiment, two such windows are provided located at opposite sides of the housing 10.

Furthermore, at the proximal end 12 of the housing 10, a further window 14 is provided that is used to indicate a set dose to a user, as described in more detail below. At the proximal end 12 of housing 10, a dose knob 103 for dose setting projects distally.

Figure 2:
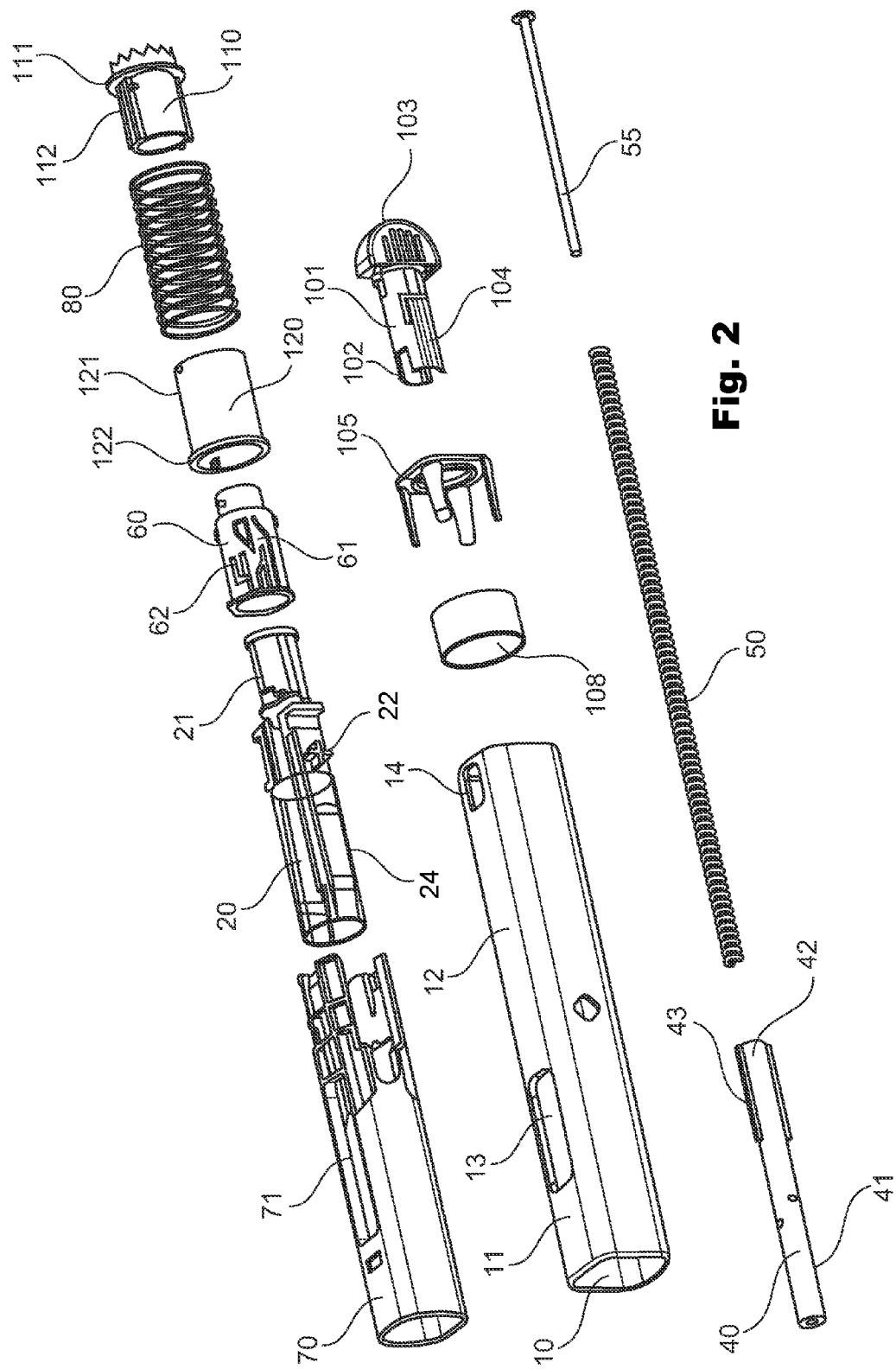
FIG. 2 shows an exploded view of the non-limiting example of the medicament delivery device of FIG. 1.

FIG. 2 shows an exploded view of the non-limiting example of the medicament delivery device 1 shown in FIG. 1. Coaxially arranged within housing 10 is a shield sleeve 70, which also comprises a window 71 that is aligned with window 13 of housing 10. The medicament delivery device 1 further comprises a medicament container holder 20 that is coaxially arranged within the shield sleeve 70. In the fully assembled state of the medicament delivery device 1, the medicament container holder 20 is at least with its proximal part located within the shield sleeve 70. The distal part 21 of the medicament container holder 20 is arranged coaxially within plunger locking means 60. The medicament container holder comprises one (or two opposing) housing connection features, such as radial protrusions 22 that allow connecting the medicament container holder 20 to the housing 10 (see also FIG. 1).

In the non-limiting embodiment shown in FIG. 2, the medicament container holder 20 comprises axial guide ribs 24. Preferably, the axial guide ribs are arranged at opposite sides of the medicament container holder 20, and extend in longitudinal direction thereof. The guide ribs 24 are received in corresponding groove structures provided at the inner surface of the proximal part of the shield sleeve 70 so that the shield sleeve 70 is axially movable in relation to the medicament container holder 20, and is also locked from being rotated relative to the housing 10 (in case of a cylindrical configuration). Plunger locking means 60 is of generally cylindrical configuration and comprises an outer groove structure 61 and a shield link lock structure 62.

FIG. 2 further shows a shield driver 120 having a distal part 121 and a shield driver flange 122 at its proximal end. Shield driver flange 122 serves as a proximal abutment surface for the first resilient member or energy accumulating member 80 that is at least with its proximal part coaxially arranged around the outer surface of shield driver 120. In the loaded state of the medicament delivery device, the first resilient member 80 is fully surrounding the shield driver 120. The first resilient member, for example a spring, is used to axially move the shield driver 120 in order to perform a priming of the medicament delivery device 1 and to initiate delivery of the medicament.

FIG. 2 also shows a plunger assembly comprising a plunger rod 40, a second resilient member 50 (such as a spring), and a plunger rod guide rod 55. These three elements are coaxially arranged in that the second resilient member 50 is at least with its proximal part received in a central bore of the plunger rod 40. Furthermore, the plunger rod guide rod 55 extends into the distal part of the second resilient member 50.

The plunger rod comprises the plunger rod proximal end 41 and a plunger rod distal end 42. At least one plunger rod stop rib 43 is arranged at the outer surface of the plunger rod 40 at its distal part 42. For example, two such ribs are provided spaced at 180° to each other. These plunger rod stop ribs 43 extend axially, i.e. in longitudinal direction of the medicament delivery device. The plunger rod stop rib(s) 43 is slidably receivable in corresponding grooves at the inner surface of the medicament container holder 20, as will be described below.

FIG. 2 also shows the elements of a dose setting mechanism. The dose setting mechanism comprises a dose member 101, a tubular increment element 110, an engagement element 105, and a dose drum 108.

The dose member 101 comprises a proximal dose member engagement part 102 with outer rotational lock structure 104, and dose knob 103 at its distal end. Dose knob 103 is gripped by a user for setting a dose by rotating the dose knob 103. Such rotation is transferred via the proximal dose member engagement part 102 to other components of the medicament delivery device 1. The rotational lock structure 104 interacts with a corresponding lock structure at the inner surface of the tubular increment element 110. The tubular increment element 110, in turn, comprises at its outer surface a shield link lock structure 112 that engages with a corresponding lock structure at the inner surface of the shield driver 120.

The tubular increment element 110 further comprises a circumferential ledge 111, which serves as a distal abutment surface for the first resilient member 80. Alternatively, the first resilient member 80 may be in contact with a ledge provided at the inside of the distal housing part, proximal to the ledge of the tubular increment element 110. Furthermore, the shield sleeve 70 abuts with its distal surface against the shield driver flange 122 of the shield driver 120.

Figure 3:
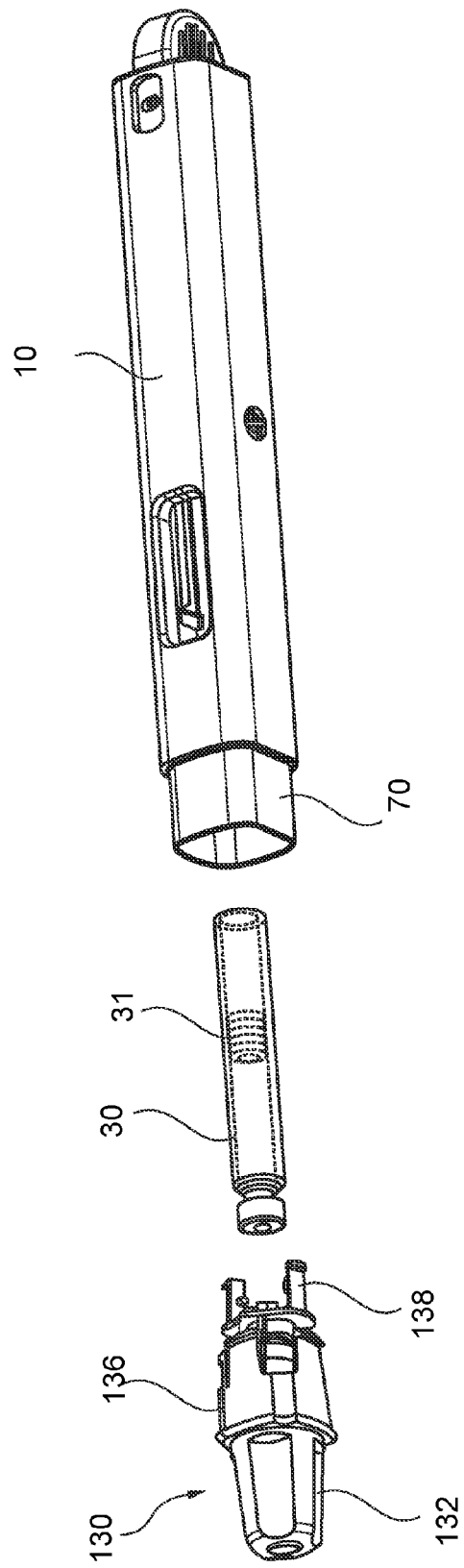
FIG. 3 shows a partly exploded view of the non-limiting example of the medicament delivery device of FIG. 1.

FIG. 3 shows a partly exploded view of a medicament delivery device prior to full assembly according to the preferred embodiment of the invention. In addition to the elements already shown in FIG. 1, FIG. 3 shows a medicament container 30 with an internal stopper 31.

Figure 4:
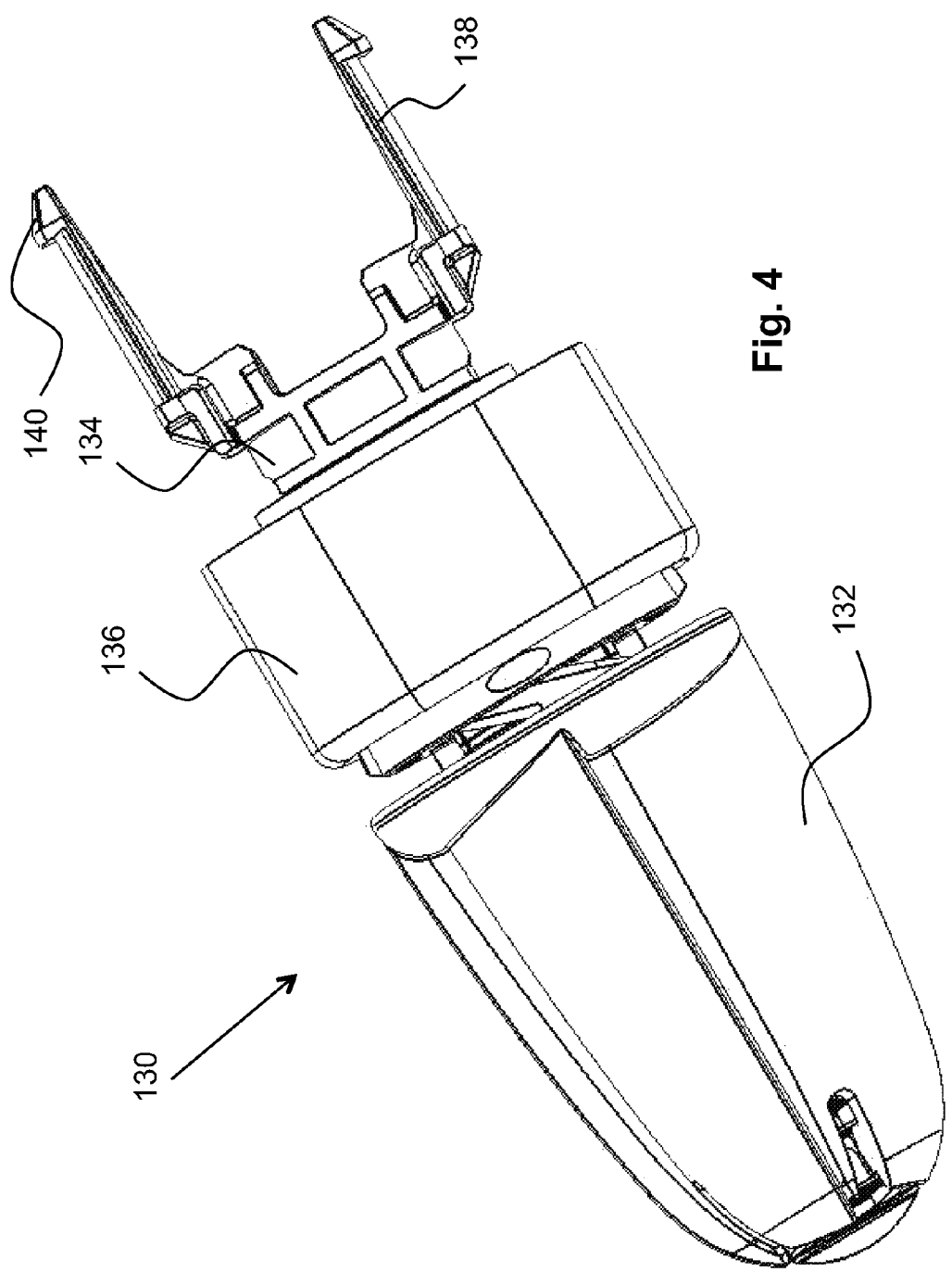
FIG. 4 is a side view of an embodiment of a cap assembly according to the present invention.
Figure 5:
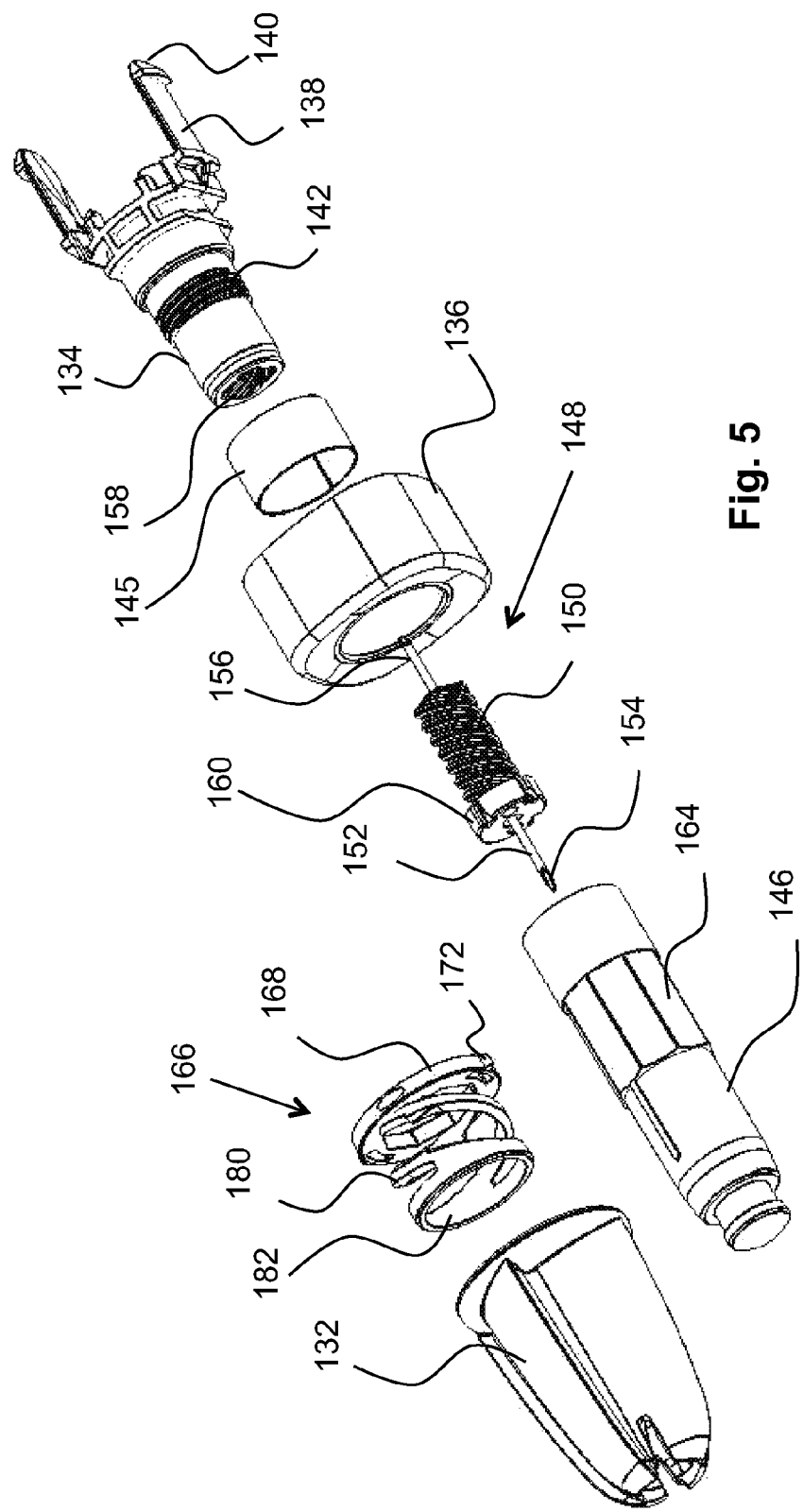
FIG. 5 is an exploded view of the embodiment of FIG. 4.

FIG. 3 also shows a cap assembly 130 according to the present invention to be connected to a medicament delivery device such as the one shown in FIG. 1. The cap assembly according to the present invention comprises, among other elements, a removable outer cap 132, a retainer member 134, a removable inner cap 146, a shield front 136 and a cap clutch mechanism 166 comprising a locking member 168, FIG. 4, which is axially movable in relation to said inner and outer caps between a disengaged position in which said locking member is disconnected from the outer and the inner cap such that the outer cap is rotatable in relation to said inner cap and an engaged position in which said locking member is connected to the outer and to the inner cap such that the outer cap is rotationally locked to the inner cap. A distal surface 137, FIG. 7, of the shield front 136 is intended to be connected to the proximal end of the shield sleeve 70. The retainer member 134 is arranged with distally extending locking structures that in the embodiment shown comprises at least two distally directed arms 138 having flexing properties in the generally radial direction of the retainer member 134. Further, the distal ends of the arms 138 are arranged with outwardly directed ledges 140, which ledges 140 are intended to, in the assembled state, be fixedly connected to the medicament container holder 20. The retainer member 134 is further arranged with an outer thread structure 142, FIG. 5, provided with threads that have a certain pitch. This thread structure is arranged to interact with corresponding thread structure 144 on an inner distal cylindrical surface of the inner cap 146, FIG. 6. A spacer ring 145 is further arranged to be positioned between the retainer member 134 and the inner cap 146 when the latter is threaded onto the retainer holder, as seen in FIG. 7.

Inside the inner cap 146, a hub 148 is arranged. The hub 148 is provided with an engagement member 150 on its outer surface, in the shown embodiment as threads. An injection needle 152 is attached to the hub and extending through it, providing a proximal needle end 154 and a distal needle end 156. The engagement member 150 of the hub 148 is intended to cooperate with a corresponding engagement member 158, FIG. 5, on an inner cylindrical surface of the retainer member 134, in the embodiment shown corresponding threads. The threads 150 of the hub 148 and the corresponding threads 158 on the retainer member 134 have a pitch and direction on the threads that are opposite as the threads 142 of the retainer member 134 and the threads 144 on the inner cap 146, as will be explained below. The hub 148 is further arranged with longitudinally extending slits 160, FIG. 5, which slits 160 are designed to cooperate with longitudinally extending ribs 162 on the inner surface of the inner cap 146, FIG. 6, such that the hub 148 is rotationally locked, but slidable, in relation to the inner cap 146. At a distal end of the inner cylindrical surface of the retainer member, a barrier 163 is further provided, FIGS. 6 and 7, which will act as a sterile barrier together with the threadedly engaged hub 148 in the retainer member 134 for the distal end 156 of the injection needle.

Figure 6:
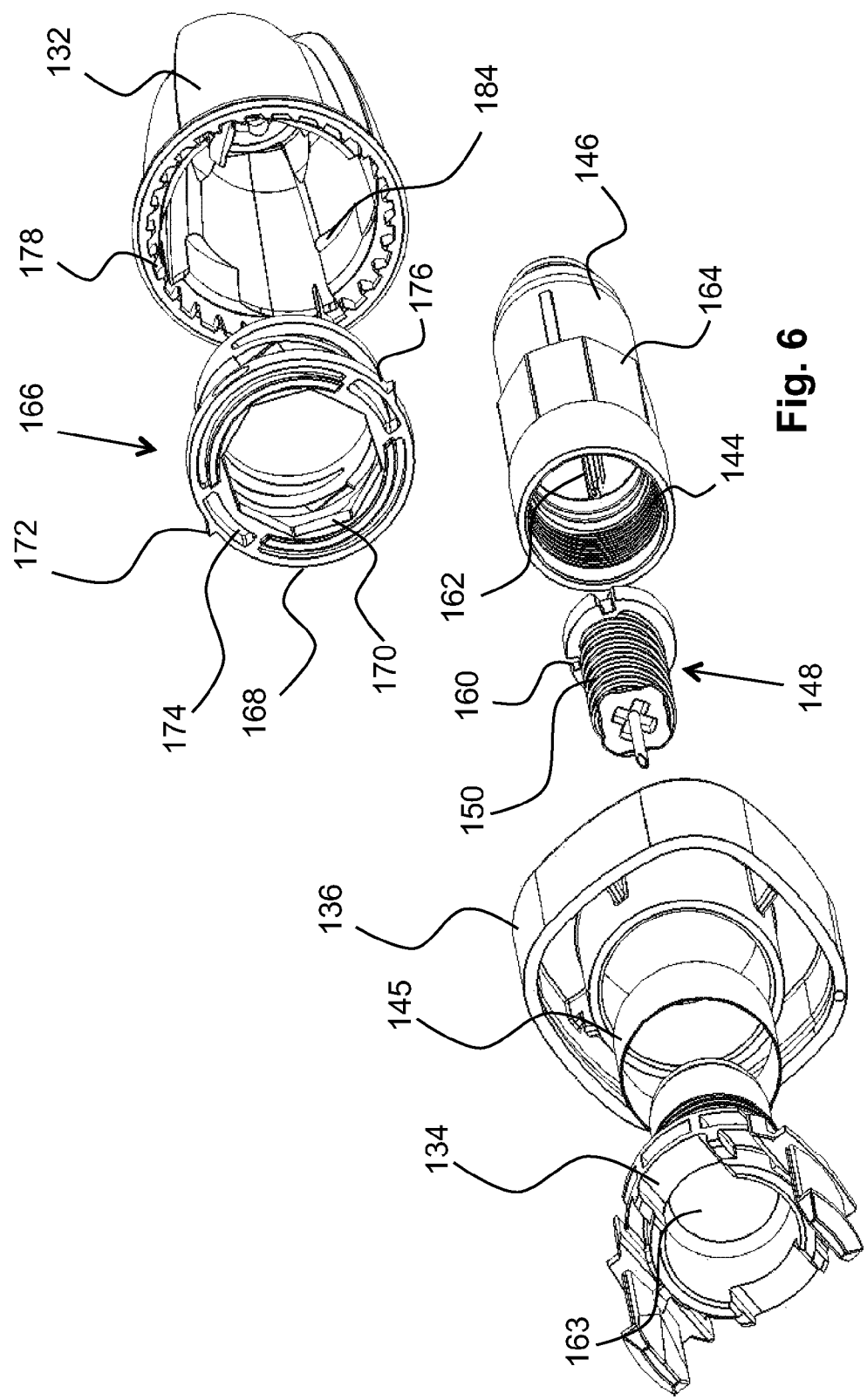
FIG. 6 is an exploded view similar to the view of FIG. 4 but turned approximately 180 degrees.
Figure 7:
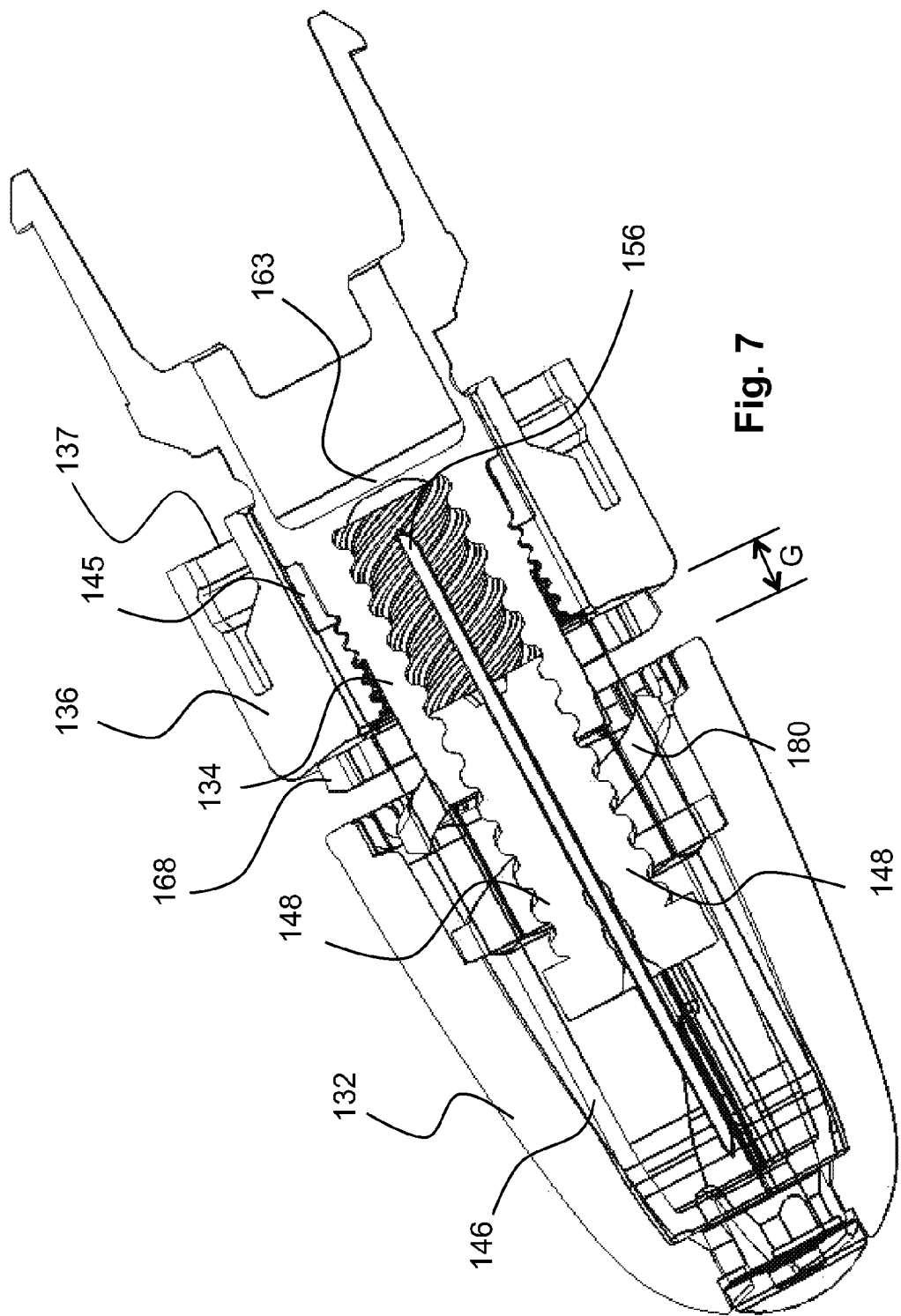
FIGS. 7 to 9 are cross-sectional side views of the embodiment of FIG. 4 during different operational steps.

The outer surface of the inner cap 146 is arranged with a number of planar surfaces 164, FIG. 6, forming the appearance of a nut. These surfaces 164 are arranged to cooperate with an outer cap clutch mechanism 166, FIG. 5, comprising a ring-shaped locking member 168, FIGS. 5 and 6, where the inner surface of the locking member 168 is arranged with planar surfaces 170, FIG. 6, such that the locking member 168 fits together with the nut 164 of the inner cap 146 to form a rotational lock between the two components. The locking member 168 is further provided with first engagement members that in the embodiment shown comprise radially outwardly extending protrusions 172 FIG. 6, on the outer surface, where the protrusions 172 have a generally wedge-shape as seen in a proximal or distal direction. Radially inwards of the protrusions 172, the locking member 168 is arranged with cut-outs 174 so as to form a flexible land or bridge 176, FIG. 6, of material on which the protrusions 172 are attached.

The protrusions 172 of the locking member 168 are arranged to cooperate with second engagement members in the form of a ratchet 178 arranged on an inner surface of the outer cap 132 at its distal area, FIG. 6. The ratchet 178 preferably has a shape that forms a wedge-shape as seen from the distal direction. The protrusions 172 and the ratchet 178 are thus intended to cooperate such that the outer cap 132 can only bring the locking member 166 with it in one direction. In the opposite direction, the ratchet 178 will slide over the protrusions 172, whereby the latter will flex in the radial direction due to the flexible land 176.

The cap clutch mechanism 166 further comprises clutch biasing means 180 arranged between the outer cap 132 and the locking member 168, said clutch biasing means is capable of biasing the locking member for keeping it in the disengaged position. The clutch biasing means 180 is a resilient member. In the embodiment shown in FIG. 5, the resilient member comprises a distal end that is fixedly connected to, or integrated with, the locking member and a proximal end configured to abut against an abutting surface on the inner surface of the outer cap. In the embodiment shown in FIG. 5, the resilient member has a spiral shape and is integral with the locking member. It is to be understood that the embodiment described the drawing is to be regarded only as a non-limiting example and that it may be modified in many ways such as having a resilient member which is only abutting the locking member and not being fixedly connected to it. The proximal end of the locking member 180 is preferably attached to, or integrated with, a contact member 182, in the embodiment shown as a ring. The contact member 182 is intended to be seated in a ledge 184 on the inner surface of the outer cap 132.

When the cap assembly is assembled as seen in FIG. 7, the locking member 168 is in the disengaged position in which said locking member is disconnected from the outer and the inner cap such that the outer cap is rotatable in relation to said inner cap, i.e. the outer cap 132 is out of engagement with the locking member 168 since the resilient member is urging the locking member 168 in the distal direction against a proximal surface of the shield front 136. There is a gap or distance G between the distal end surface of the outer cap 132 and the shield front 136 as seen in FIG. 7.

Figure 8:
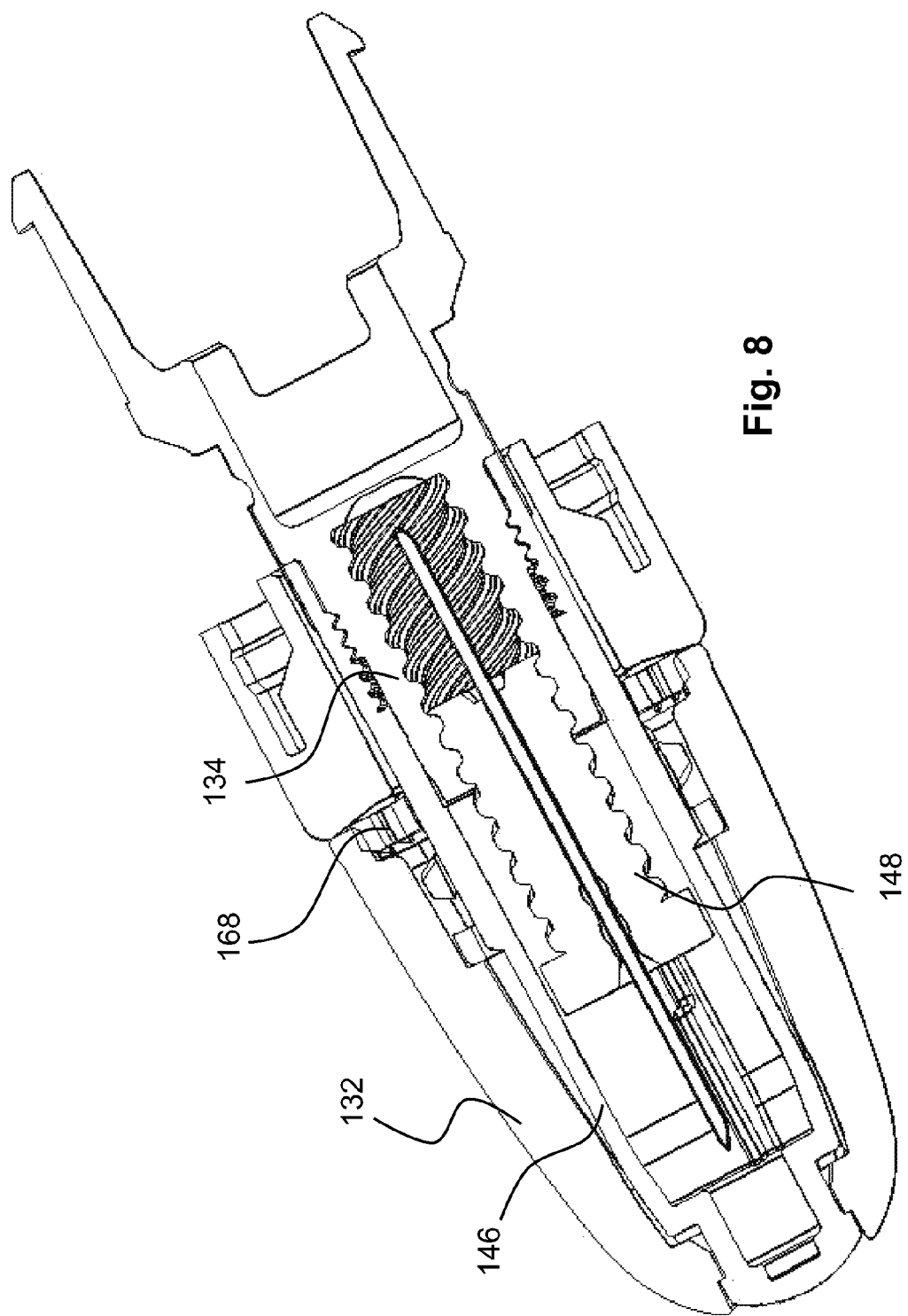

During normal use, when a patient is to use the medicament delivery device for delivering a dose of medicament, the dose knob 103 is maneuvered. This in turn causes the shield driver 120 to be released from its initial position by the energy accumulating member 80 which is fully loaded. The shield driver 120 moves in the proximal direction due to the force of the energy accumulating member 80, whereby the shield sleeve 70 and thus the shield front 136 are also moved. The movement of the shield front 136 in the proximal direction further causes the locking member 168 to move in the proximal direction against the force of the resilient member of the cap clutch mechanism 166, i.e. the locking member is moved from the disengaged position to the engaged position in which said locking member is connected to the outer and to the inner cap such that the outer cap is rotationally locked to the inner cap. After the movement is completed, the first and second engagement members 172, 178 are in contact with each other, FIG. 8. When a user now actively turns the outer cap 132 (e.g., in counterclockwise direction) in order to remove it from the medicament delivery device, due to a respective engagement of the outer cap 132 with the inner cap 146, turning of the outer cap 132 to remove it proximally causes the hub 148 to be screwed distally into the retainer member 134 whereby the pointed distal end 156 of the needle 152 penetrates the sterile barrier 163 and subsequently the membrane of the medicament container 30. Finally, the outer cap 132 and the inner cap 146 can be removed.

Preferably, the pitches of the threads are chosen such that there is a major longitudinal movement of the hub 148 in the distal direction for a small turning angle in order to prevent as much as possible turning or "drilling" of the distal end 156 of the needle 152 in the membrane of the medicament container 30. At the same time, the pitch of the threads between the outer cap 132 and the retainer member 134 is preferably chosen such that the user only needs to turn the outer cap 132 about half a turn in order to perform the removal operation so as to avoid having to change grip in order to finish the operation.

Figure 9:
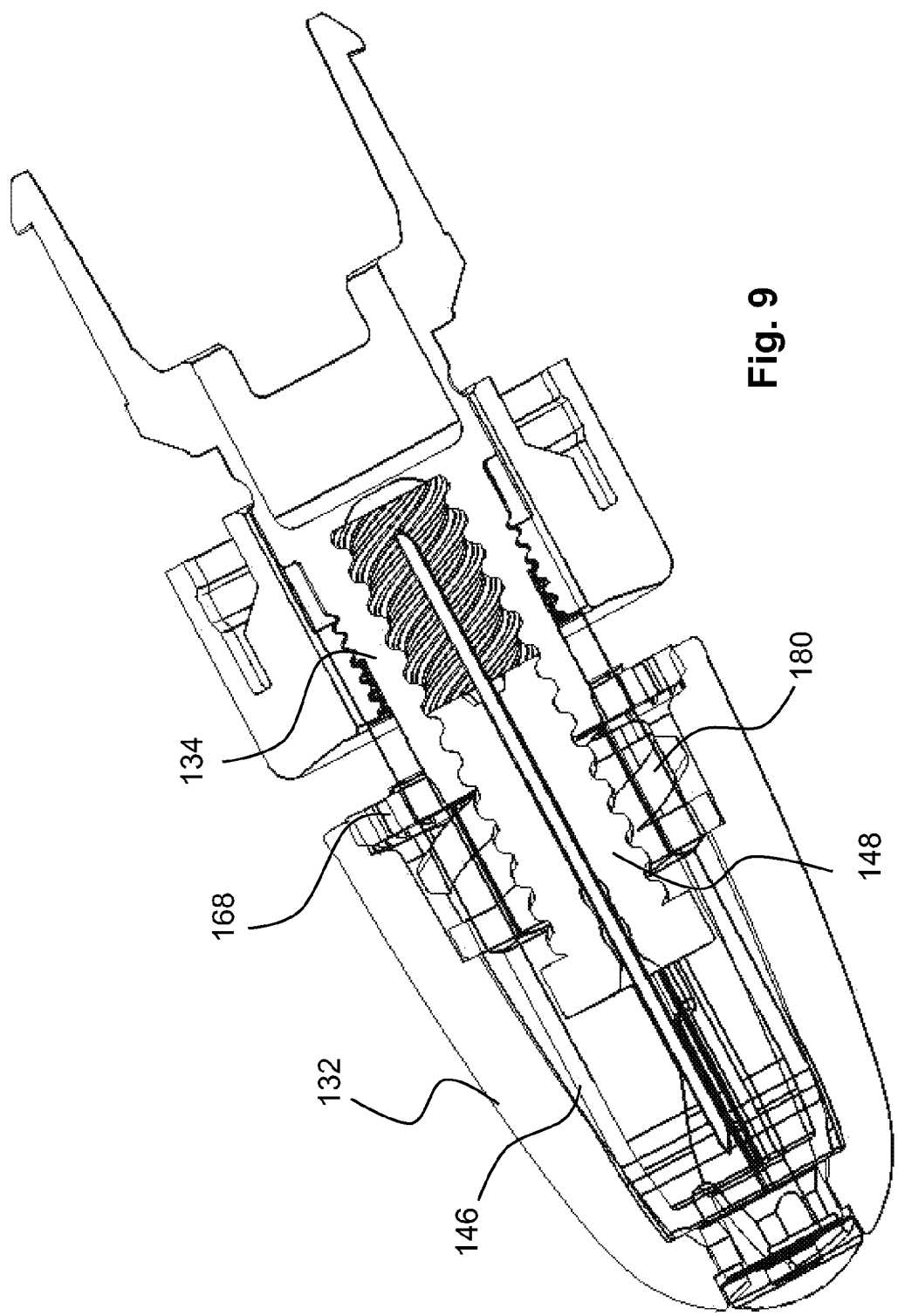

If however the cap assembly should be exposed to a sudden external force, such as if e.g. the medicament delivery device was dropped with its proximal end on a hard surface, such as a floor, the locking member 168 of the clutch mechanism 166 would be urged in the proximal direction and into engagement with the outer cap 132, as seen in FIG. 9. However, thanks to the resilient member of the cap clutch mechanism 166, the locking member 168 is urged back to its original position out of engagement as soon as the external force is reduced or removed. Thus, after an exposure to external forces, the cap assembly is reset to original safety position again.

It is to be understood that the embodiment described above and shown in the drawings is to be regarded only as a non-limiting example of the invention and that it may be modified in many ways within the scope of the patent claims.

The invention claimed is:

1. A cap assembly for a medicament delivery device that has a housing and a medicament container holder, the cap assembly comprising:
   a retainer member for connection to the medicament container holder;
   a hub, comprising a needle having a proximal end and a distal end, the hub being coaxially movable within the retainer member;
   a removable inner cap interactively connected to the hub and to the retainer member;
   a removable outer cap coaxially arranged to the inner cap; and
   a cap clutch mechanism, comprising a locking member and a clutch biasing device, wherein the locking member is axially movable in relation to the inner and outer caps between a disengaged position, in which the locking member is disconnected from the inner and outer caps such that the outer cap is rotatable in relation to the inner cap, and an engaged position, in which the locking member is connected to the inner and outer caps such that the outer cap is rotationally locked to the inner cap; and the clutch biasing device is arranged between the outer cap and the locking member for biasing the locking member to keeping the locking member in the disengaged position.

2. The cap assembly of claim 1, wherein the locking member comprises a passage having a number of first planar surfaces, the inner cap comprises a number of second planar surfaces on its outer surface, and the first and second planar surfaces form a rotational lock when the locking member is in the engaged position.

3. The cap assembly of claim 1, wherein the clutch biasing device is a resilient member.

4. The cap assembly of claim 3, wherein the resilient member comprises a distal end that is fixedly connected to the locking member and a proximal end configured to abut against an abutting surface on the inner surface of the outer cap.

5. A cap assembly for a medicament delivery device that has a housing and a medicament container holder, the cap assembly comprising:
  a retainer member for connection to the medicament container holder;
  a hub, comprising a needle having a proximal end and a distal end, the hub being coaxially movable within the retainer member;
  a removable inner cap interactively connected to the hub and to the retainer member;
  a removable outer cap coaxially arranged to the inner cap; and
  a cap clutch mechanism, comprising a locking member and a clutch biasing device, wherein the locking member is axially movable in relation to the inner and outer caps between a disengaged position, in which the locking member is disconnected from the inner and outer caps such that the outer cap is rotatable in relation to the inner cap, and an engaged position, in which the locking member is connected to the inner and outer caps such that the outer cap is rotationally locked to the inner cap; and the clutch biasing device is arranged between the outer cap and the locking member for biasing the locking member to keeping the locking member in the disengaged position;
  wherein the clutch biasing device is a resilient member, the resilient member comprises a distal end that is fixedly connected to the locking member and a proximal end configured to abut against an abutting surface on the inner surface of the outer cap, and the resilient member has a spiral shape and is integral with the locking member.

6. The cap assembly of claim 1, wherein the locking member comprises a number of first engagement members configured to interact with a number of corresponding second engagement members on the outer cap when the locking member is in the engaged position.

7. The cap assembly of claim 6, wherein the locking member comprises a passage having a number of first planar surfaces, the inner cap comprises a number of second planar surfaces on its outer surface, and the first and second planar surfaces form a rotational lock when the locking member is in the engaged position.

8. The cap assembly of claim 6, wherein the clutch biasing device is a resilient member.

9. The cap assembly of claim 8, wherein the resilient member comprises a distal end that is fixedly connected to the locking member and a proximal end configured to abut against an abutting surface on the inner surface of the outer cap.

10. The cap assembly of claim 9, wherein the resilient member has a spiral shape and is integral with the locking member.

11. The cap assembly of claim 6, wherein the first and second engagement members enable engagement between the outer cap and the inner cap in only one rotational direction.

12. The cap assembly of claim 11, wherein the locking member comprises a passage having a number of first planar surfaces, the inner cap comprises a number of second planar surfaces on its outer surface, and the first and second planar surfaces form a rotational lock when the locking member is in the engaged position.

13. A cap assembly for a medicament delivery device that has a housing and a medicament container holder, the cap assembly comprising:
  a retainer member for connection to the medicament container holder;
  a hub, comprising a needle having a proximal end and a distal end, the hub being coaxially movable within the retainer member;
  a removable inner cap interactively connected to the hub and to the retainer member;
  a removable outer cap coaxially arranged to the inner cap; and
  a cap clutch mechanism, comprising a locking member and a clutch biasing device, wherein the locking member is axially movable in relation to the inner and outer caps between a disengaged position, in which the locking member is disconnected from the inner and outer caps such that the outer cap is rotatable in relation to the inner cap, and an engaged position, in which the locking member is connected to the inner and outer caps such that the outer cap is rotationally locked to the inner cap; and the clutch biasing device is arranged between the outer cap and the locking member for biasing the locking member to keeping the locking member in the disengaged position;
  wherein the locking member comprises a number of first engagement members configured to interact with a number of corresponding second engagement members on the outer cap when the locking member is in the engaged position, the first and second engagement members enable engagement between the outer cap and the inner cap in only one rotational direction, the first engagement member comprises a number of wedge-shaped protrusions on the locking member, and the second engagement member comprises a ratchet on the outer cap.

14. The cap assembly of claim 13, wherein the locking member comprises a passage having a number of first planar surfaces, the inner cap comprises a number of second planar surfaces on its outer surface, and the first and second planar surfaces form a rotational lock when the locking member is in the engaged position.

15. The cap assembly of claim 14, wherein the clutch biasing device is a resilient member.

16. The cap assembly of claim 15, wherein the resilient member comprises a distal end that is fixedly connected to the locking member and a proximal end configured to abut against an abutting surface on the inner surface of the outer cap.

17. The cap assembly of claim 16, wherein the resilient member has a spiral shape and is integral with the locking member.

18. The cap assembly of claim 1, further comprising a shield front for connection to a proximal end of an axially movable shield sleeve of the medicament delivery device.

19. A medicament delivery device, comprising a cap assembly according to claim 1.

* * * * *